United States Patent [19]
Beavers et al.

[11] Patent Number: 6,106,889
[45] Date of Patent: Aug. 22, 2000

[54] METHOD OF SELECTIVE COATING OF ARTICLES

[75] Inventors: Ellington M. Beavers, Meadowbrook; Elizabeth G. Pervin, Philadelphia, both of Pa.

[73] Assignee: Biocoat Incorporated, Fort Washington, Pa.

[21] Appl. No.: 09/096,288

[22] Filed: Jun. 11, 1998

[51] Int. Cl.[7] .............................. B05D 1/32; B05D 3/00
[52] U.S. Cl. ........................ 427/2.1; 427/2.3; 427/155; 427/259; 427/264; 427/272; 427/336; 2/161.7; 2/167; 424/429; 604/265; 604/915
[58] Field of Search .................... 427/2.12, 2.24, 427/2.28, 2.3, 259, 264, 265, 261, 272, 282, 154, 155, 2.1, 336, 353; 2/161.7, 167; 424/429; 604/265, 915

[56] References Cited

U.S. PATENT DOCUMENTS

| | | | |
|---|---|---|---|
| 3,853,576 | 12/1974 | Netznik | 427/154 |
| 3,926,705 | 12/1975 | Todd | 156/155 |
| 3,935,334 | 1/1976 | Narui et al. | 427/272 |
| 4,170,661 | 10/1979 | Knight et al. | 427/2.1 |
| 4,311,146 | 1/1982 | Wonder | 427/2.3 |
| 4,447,227 | 5/1984 | Kotsanis | 604/95 |
| 4,666,249 | 5/1987 | Bauman et al. | 351/160 |
| 4,670,313 | 6/1987 | Saudagar | 428/12 |
| 4,696,065 | 9/1987 | Elenteny | 2/168 |
| 4,720,315 | 1/1988 | Greenman | 427/272 |
| 4,748,049 | 5/1988 | Charles et al. | 427/336 |
| 4,801,475 | 1/1989 | Halpern et al. | 427/338 |
| 4,886,704 | 12/1989 | Kamada et al. | 427/259 |
| 5,023,114 | 6/1991 | Halpern et al. | 427/338 |
| 5,030,290 | 7/1991 | Davis | 427/156 |
| 5,037,677 | 8/1991 | Halpern et al. | 427/338 |
| 5,061,738 | 10/1991 | Solomon et al. | 427/2.3 |
| 5,143,949 | 9/1992 | Grogan et al. | 523/334 |
| 5,370,900 | 12/1994 | Chen | 427/2.3 |
| 5,409,731 | 4/1995 | Nakagawa et al. | 427/2.12 |
| 5,411,760 | 5/1995 | Woodhall et al. | 427/259 |
| 5,429,838 | 7/1995 | Mansson et al. | 427/2.24 |
| 5,503,631 | 4/1996 | Onishi et al. | 604/96 |
| 5,513,791 | 5/1996 | Rowe et al. | 228/118 |
| 5,688,855 | 11/1997 | Stoy et al. | 524/505 |
| 5,713,986 | 2/1998 | Franz et al. | 427/154 |
| 5,725,875 | 3/1998 | Noll et al. | 424/445 |
| 5,736,251 | 4/1998 | Pinchuk | 427/387 |
| 5,741,429 | 4/1998 | Donadio, III et al. | 216/8 |
| 5,746,745 | 5/1998 | Abele et al. | 606/108 |
| 5,789,018 | 8/1998 | Engelson et al. | 427/2.28 |
| 5,902,631 | 5/1999 | Wang et al. | 427/2.1 |
| 5,910,518 | 6/1999 | Nakada et al. | 427/2.1 |
| 5,948,545 | 7/1999 | Svensson | 427/336 |

*Primary Examiner*—Diana Dudash
*Attorney, Agent, or Firm*—William H. Eilberg

[57] ABSTRACT

Articles such as medical devices are selectively coated with a lubricious coating. A temporary coating, formed from an aqueous solution of a water-soluble polymer of low to moderate molecular weight, is painted onto those portions of the article which are to remain free of any coating in the final product. Then, the entire article is coated with a material which forms a lubricious coating. The article is then soaked in water to loosen the coatings at the locations at which the temporary coating was applied. The coatings are cleanly removed from those locations, leaving an article with a lubricious coating in some portions, and which is uncoated in the remaining portions. The process can be used in coating portions of catheters, surgical gloves, contact lenses, and any other articles which require a lubricious coating only on a portion of the surface of the article.

9 Claims, No Drawings

METHOD OF SELECTIVE COATING OF ARTICLES

BACKGROUND OF THE INVENTION

The present invention relates to the field of coating of articles, especially medical products and/or medical devices.

The application of biocompatible, lubricious coatings to medical devices is well known and widely practiced. Examples of patents discussing the coating of such devices include U.S. Pat. Nos. 4,801,475, 5,023,114, and 5,037,677, the disclosures of which are hereby incorporated by reference herein.

Whether the coating is applied by dipping, spraying, or other means, the surface is normally coated with a continuous film, i.e. without "skipping" areas.

The coatings described above may be temporary hydrogels, less fugitive polymers of N-vinylpyrrolidone, or firmly attached and abrasion-resistant products such as those known commercially by the trademark HYDAK with grafted mucopolysaccharide surfaces. The HYDAK product is available from Biocoat Incorporated, of Fort Washington, Pa. HYDAK is a registered trademark of Biocoat Incorporated.

The preferred method of applying such coatings is withdrawal from a dipping bath at controlled speeds, the coating thickness so produced being a consequence of the withdrawal speed, the viscosity of the material being applied, and other factors. The overall result is a desirably uniform, continuous, and durable coated surface.

However, with certain devices, such as a balloon catheter that is intended to aid in the placement of stents in the vascular system, it is highly desirable that most of the length of the catheter be coated with a non-thrombogenic, slippery material, while the balloon(s) should not be slippery. The reason for coating the catheter body but not the balloon is that if the balloon surface is also slippery, the stent riding on it may slip out of place prematurely before it is properly placed. On some such interventional catheters, there may even be two or more balloons on the same catheter, spaced apart on a multilumined catheter shaft. On a sixty-inch catheter, two or more balloons may be located near the distal end and spaced only a short distance apart.

The primary purpose of the multiple-balloon arrangement is to enable the radiologist to carry out more than one diagnostic or remedial function without having to perform catheter insertions more than once. Thus, the foremost advancing balloon might be employed to expand the blood vessel in the area of constriction. A lubricious, hydrophilic surface on this balloon is usually highly desirable. The second balloon may be carrying a stent to be placed in the expanded area of the blood vessel to retard or prevent re-stenosis. The surface of the second balloon should hold the stent securely until the point of deposit is reached. The surface of this second balloon, which is called the "transport balloon", should not be slippery.

The dipping process for coating catheters and guide wires does not provide any obvious means of accomplishing the selective coating of different sections of the device. Normally, the length of the device to be coated is immersed in the coating bath and then withdrawn at a carefully controlled rate, so that the entire length is uniformly covered with a film of the desired thickness. In this process, there is no way of discontinuing the deposition precisely when the edge of the transport balloon is reached, and of resuming the deposition precisely when its trailing edge has passed.

The above-described problem might be solved by choosing some other method of applying the coating than dipping, but the alternatives have their own problems. Spray coating, for example, is labor-intensive, and expensive to apply to individual catheters, and in addition is capable of painting the precise margins at the leading and trailing edges of the transport balloon only when applied by an artist with special "spray pens". Another solution is to fabricate and attach the transport balloon after the remainder of the catheter has been coated. But the latter process has the disadvantage that coating of the catheter tends to plug the air port from the lumen at the site of the balloon to be mounted later. There are still other alternatives that could be devised, but each has its own negative features.

The above-described problem is not limited to catheters, but is encountered with other medical devices, as will be described later.

The present invention provides a method which solves the above problem in an economical, practical, and effective way. The present invention provides a method for selective coating of a wide variety of medical products and devices. The invention can also be used to coat other articles where selective coating is desirable.

SUMMARY OF THE INVENTION

The present invention comprises a method of selectively coating an article, especially a medical device, with a lubricious coating. That is, the lubricious coating is present, in the final product, only at desired locations on the article.

According to the method of the invention, one first applies a temporary coating to selected portions of the article. Those selected portions comprise the areas in which a permanent coating is not desired. Next, one coats the entire article with a second coating, the second coating comprising a material which forms a lubricious coating. Finally, one removes the first and second coatings only at those locations corresponding to the portions that were coated with the temporary coating. Removal of these coatings is made easy by first soaking the article in water. The coatings can then be easily removed manually. The lubricious coating remains firmly attached to those portions of the article which did not receive the temporary coating.

The temporary coating comprises a solution of a water-soluble polymer of low to moderate molecular weight. The water-soluble polymer may be selected from the group consisting of polyvinyl alcohol, polyvinylpyrrolidone, hydroxypropylmethyl cellulose, gelatin, chondroitin sulfate, sodium polyacryl ate, poly(N,N-dimethylacrylamide), soluble starch, and polyethyleneoxides. The concentration of the solution may be in a range of about 1–15 percent, and more preferably in a range of about 1–5 percent.

The invention therefore has the primary object of providing a method for selective coating of articles.

The invention has the further object of providing a method wherein one can apply a lubricious coating only to selected portions of an article.

The invention has the further object of providing a method which makes it easy to coat part of a medical device with a lubricious coating, while leaving the remainder of the device uncoated.

The invention has the further object of improving the efficiency of manufacture of medical devices and products, such as catheters, surgical gloves, and contact lenses.

The invention has the further object of improving the quality and utility of medical devices, without significantly increasing their cost.

The reader skilled in the art will recognize other objects and advantages of the present invention, from a reading of the following detailed description of the invention, and the appended claims.

DETAILED DESCRIPTION OF THE INVENTION

In its most general form, the method of the present invention comprises painting a portion of the surface of an article with a temporary coating comprising a solution of a water-soluble polymer of low to moderate molecular weight. The temporary coating is painted onto those parts of the surface which are intended to have no coating in the final product. The temporary coating is then dried. The article is then dip-coated in the usual manner, with a hydrophilic coating of choice, and then dried and cured. Later, the article or a portion thereof is soaked briefly in water, and the entire coating on the area where the temporary coating was applied is lifted off cleanly. The result is an article having a lubricious coating on certain portions, and no coating at all on the remaining portions.

The water-soluble polymer used to form the temporary coating should be low in cost, readily available, non-corrosive, and non-toxic. Otherwise, the choice of the polymer is not of critical importance. Examples of polymers that can be used are polyvinyl alcohol, polyvinylpyrrolidone, hydroxypropylmethyl cellulose, gelatin, and chondroitin sulfate. Others are sodium polyacrylate, poly(N,N-dimethylacrylamide), soluble starch, and polyethyleneoxides. The molecular weight of the polymer should be high enough so that the wet polymer has enough strength and film integrity to peel off in one piece, and low enough so that the soaking time required to relax adhesion to the catheter surface is short. The concentration of the polymer solution may be in the range of less than one percent to more than fifteen percent, but preferably is in the range of about 1–5 percent. All concentrations in this specification are by weight.

The value implied by the expression "low to moderate molecular weight" varies with the polymer. Some polymers, such as chondroitin sulfate may occur in nature with a molecular weight as high as 25,000, while others, such as hydroxypropylmethyl cellulose might be as high as 1,000,000. Hyaluronate may have a molecular weight as great as 8,000,000. The term "low to moderate" therefore means low to moderate relative to the highest molecular weight at which the polymer exists. Apart from the definition of low to moderate molecular weight, an important property of the watersoluble polymer in this invention is that it rapidly imbibes water and softens and/or dissolves.

The following examples show the use of the present invention in coating various devices.

EXAMPLE 1

In this Example, the article being coated is a material which simulates that of a balloon on a commercial percutaneous transluminal coronary angioplasty (PTCA) catheter. The balloon is typically made of polyester. The purpose of this Example is to demonstrate the performance of various solutions listed below in Table 1 as candidates for the temporary coating. In each case, the balloon material was first coated with the temporary coating. Then, the entire material was dip-coated with HYDAK G-23 and sodium hyaluronate, simulating the commercial practice with PTCA catheters. The HYDAK and sodium hyaluronate form a lubricious coating. When the lubricious coating was dried and cured, the coated material was soaked in water for the times indicated in the table, and removal of the coating from the material was attempted by hand. The results are listed in the table.

TABLE 1

| Polymer | Concentration | Viscosity (Stokes) | Ease of Removal after One Hour | Ease of Removal after Three Hours |
|---|---|---|---|---|
| PVP-8M | 15.8% | 4.8 | Tightly held | Poor release |
| PVP-LoM | 14.4 | 0.25 | Loosening | Peels with effort |
| PVAlc-10M | 9.0 | 5.3 | — | Peels with effort |
| PVAlc-LoM | 14.1 | 1.7 | Peels with effort | Peels easily |
| PVAlc-LoM | 10.0 | 0.5 | Peels | |
| PVAlc-LoM | 5.0 | 0.2 | Peels spontaneously | |

PVP-8M = Polyvinylpyrrolidone, molecular weight 8,000 daltons
PVP-LoM = Polyvinylpyrrolidone of lower molecular weight
PVAlc-10M = Polyvinyl alcohol, molecular weight 10,000 daltons
PVAlc-LoM = Polyvinyl alcohol of lower molecular weight Table 1 shows the favorable results obtained from polymers of lower molecular weight and lower concentration.

EXAMPLE 2

The last three lines of Table 1, above, show the effect of concentration of the polyvinyl alcohol, at approximately constant molecular weight. This Example demonstrates the effect of varying the molecular weight of the polyvinyl alcohol, while maintaining the concentration constant. The procedure for this Example was the same as in Example 1, the only differences being in the materials used for the temporary coating. The results are shown in Table 2, below.

TABLE 2

| PV Alcohol Grade | Viscosity | Concentration | Minimum Soaking Time to Peel |
|---|---|---|---|
| 51-05 | 4–6 | 2.5% | Less than 30 seconds |
| 52-22 | 21–25 | 2.5% | 1 minute |
| 50-42 | 35–45 | 2.5% | 7 hours |

The viscosities above are in centipoises of 4% aqueous solutions at 20 C. Table 2 shows that polyvinyl alcohol of low or moderate molecular weight yields the desired result, i.e. peeling after a relatively short soaking time.

EXAMPLE 3

Because the experiments described in the above examples are time-consuming, a more rapid screening test was devised. In this test, blocks of PMMA plastic, having dimensions of 0.6×2×3 cm were marked with a transverse line 1.5 cm from the end of each block. The weight of each block was 4.38+/−0.06 grams. The blocks were numbered for identification on one side of the line.

Strips 3 cm long by 2 cm wide were cut from Spectra/Mesh netting made of polypropylene and having grid openings of 1.5 mm and a net thickness of 0.48 mm.

One of the PMMA blocks was immersed up to the transverse line in an aqueous solution of a polymer of interest, and drained briefly. The block was laid flat, and a strip of the netting was placed on the upper wet surface. A stainless steel nut weighing 50 grams was laid on the joint while it dried. After a brief air-drying, the assembly was placed in an oven at 60° C. for one hour. When cool, it was ready for the test.

With an alligator clip, each test sample was held by the free end of the netting while the joint and PMMA block were totally immersed in distilled water at 20° C. The time was observed for the joint to loosen sufficiently for the block to fall free. Table 3 shows the fall-free times for a variety of water-soluble polymers tested in this way. Also shown are the times to peel when those same polymers are used in the method of this invention.

TABLE 3

| Polymer | Concentration | Fall-Free Time | Minimum Time to Peel |
| --- | --- | --- | --- |
| PV Alc 51-05 | 2.5% | Less than 30 sec. | Less than 30 sec. |
| PV Alc 52-22 | 2.5% | 4 minutes | 1 minute |
| PV Alc 50-42 | 2.5% | 7 minutes | 7 hours |
| HPMC | 2.5% | 14 minutes | 28 minutes |
| HPMC | 1% | Less than 30 sec. | 3 minutes |

The abbreviations PV Alc and HPMC mean polyvinyl alcohol and hydroxypropylmethyl cellulose, respectively.

The above Examples also show that, although the invention works best with polymers of low to moderate molecular weight, it is impossible to assign numerical ranges, for the molecular weights, which will be valid for all water-soluble polymers. For example, hydroxypropylmethyl cellulose has a molecular weight of over one million daltons, but when it and polyvinyl pyrrolidone are applied at concentrations of 2.5%, the time for HPMC to peel is shorter than for polyvinyl pyrrolidone which has a molecular weight of only 8000. Indeed, a 4% aqueous solution of hydroxypropylmethyl cellulose has a viscosity greater than 10,000 cp, much greater than the values shown in Table 2 for the various grades of polyvinyl alcohol. Thus, the term "low to moderate molecular weight" must be interpreted with respect to the specific polymer used.

EXAMPLE 4

This Example involves the coating of an angioplasty catheter having two balloons located one centimeter apart near the distal end. A 2% aqueous solution of hydroxypropyl methyl cellulose was painted onto the balloon intended to transport a stent. The coating was air-dried, and the entire catheter was then coated with HYDAK G-23 and hyaluronate and cured in standard cycles. When the catheter was immersed in water, the coating on the transport balloon began to loosen and fall away after less than 30 minutes. With little effort, the film could be pulled away cleanly in one piece, leaving the transport balloon's surface non-wettable, in marked contrast to the highly wettable and slippery surface elsewhere along the length of the catheter.

EXAMPLE 5

This Example involves the coating of latex rubber surgical gloves. A pair of such gloves were mounted on "right" and "left" porcelain hand forms. The gripping surfaces of the thumbs and fingers were painted with a 15% solution of chondroitin sulfate from shark cartilage, and dried. The entire gloves were then dip-coated with a hydrophilic, non-thrombogenic coating and cured. When the gloves were then immersed in water, the double coating on the gripping surfaces very quickly loosened and could be removed easily, leaving those areas with a high coefficient of friction and firm traction with instruments, while the major areas remained hydrophilic, non-thrombogenic, and easy-gliding over tender tissues.

EXAMPLE 6

This Example involves the coating of contact lenses. Eyestrain from prolonged wearing of contact lenses can be relieved by coating the surfaces with a hydrophilic, slippery surface film, so that even the so-called "hard" lens can be made more comfortable by reducing the work required in the normal, frequent blinking of the eyelid over the convex surface. Dipcoating is the preferred method of applying the hydrophilic coating, so that all surfaces are equally slippery. Significant disadvantages of such slippery lenses are their tendency to wander away from their ideal position on the cornea, and the difficulty experienced by the wearer in placing and removing the lens. Manipulating such coated lenses has been likened to getting a firm grip on a watermelon seed.

A liquid gelatin film of precisely controlled thickness was knifecoated onto a glass plate. Contact lenses were lowered, concave side down, into the wet film, while being held with a vacuum wand. When the rim of a lens touched the wet film, the rim became coated with a band of gelatin. The lenses so coated were dried. They were then immersed completely in the lubricious coating materials discussed above, withdrawn smoothly, and dried and cured. Afterward, when soaked in water for a few minutes, the rim coating easily came off smoothly, leaving behind an improved coated lens with an uncoated rim that sits firmly in place on the eye and can easily be removed and replaced.

When the article being treated is a catheter, the invention can be implemented in many ways, as will be apparent to those skilled in the art. Vascular catheters are usually manufactured on a production "line" comprising a team of trained operators sitting at tables in a clean room. The operators assemble by hand the catheter components fabricated and pre-assembled assembled in part at earlier stages in the manufacturing process. Before the assembled catheter goes to the coating line (which might be in the same clean room), the temporary coating can be applied and dried. The catheter is then coated with a lubricious coating, in the normal way, and upon immersion in water, removal of the coating on the transport balloon (or any other area that received a temporary coating) is simple and clean.

Still other valuable uses can be made of the novel process of precise, selective coating of objects, according to the present invention. While medical devices such as those mentioned in the above examples are particularly well-served by the process, the invention is not limited to use with this class of materials or devices. The invention may apply in any situation where one needs to hold and manipulate a tool or instrument confidently and firmly in one area, while in other areas a hydrophilic and slippery character is needed. Any articles which are capable of receiving the coatings used in the present invention, can be selectively coated in the manner discussed above.

The invention is not limited to the use of HYDAK as the lubricious coating. It is clear that any lubricious top coat can be used in the manner claimed below, provided that the lubricious top coat becomes waterinsoluble when properly formulated, applied and cured. The selectivity of this process relies upon the water sensitivity of the doubly coated "protected" areas and the water resistance of the coated areas where lubricity in the final product is the desired property.

The invention can therefore be modified in various ways. The choice of polymer for use in the temporary coating can be varied. The type of hydrophilic coating can be changed. The above-mentioned modifications, and others which will be apparent to those skilled in the art, should be considered within the spirit and scope of the following claims.

What is claimed is:

1. A method of selectively applying a lubricious coating to a catheter having at least two balloons, the catheter having a distal end, the balloons being located in a vicinity of the distal end, wherein at least one balloon is to remain uncoated, the method comprising the steps of:

a) painting a solution of a water-soluble polymer onto at least one of the balloons to form a first coating, and drying said first coating, b) coating the entire catheter, including balloons, with a solution which forms a continuous lubricious second coating, c) immersing the catheter in water, for a time sufficient to loosen the first coating from said balloon, and d) cleanly lifting off the first and second coatings from said at least one of the balloons while leaving the second coating unaffected at all other positions.

2. The method of claim 1, wherein step (a) comprises the step of selecting the water-soluble polymer to be hydroxypropyl methyl cellulose.

3. The method of claim 2, wherein the polymer is provided in an aqueous solution having a concentration of about 2%.

4. A method of selectively applying a lubricious coating to a glove, wherein at least one portion of the glove is to remain uncoated, the method comprising the steps of:

a) painting a solution of a water-soluble polymer onto at least a portion of the glove, b) coating the entire glove with a solution which forms a lubricious coating, c) immersing at least part of the glove in water, so as to loosen the coatings from the glove, and d) removing the coatings from said portion of the glove which received a coating in step (a).

5. The method of claim 4, wherein step (a) comprises the step of selecting the water-soluble polymer to be chondroitin sulfate.

6. The method of claim 4, wherein the polymer is provided in an aqueous solution having a concentration of about 15%.

7. A method of selectively applying a lubricious coating to a contact lens, the contact lens having a rim, wherein at least a portion of the rim of the contact lens is to remain uncoated, the method comprising the steps of:

a) applying a solution of a water-soluble polymer onto at least a portion of the rim of the lens and drying said solution, b) coating the entire lens with a solution which forms a continuous lubricious coating, c) immersing the lens in water, for a time sufficient to loosen the coatings from the lens, and d) cleanly lifting off the coatings from said portion of the lens which received a coating in step (a) while leaving the second coating unaffected at all other portions of the lens.

8. The method of claim 7, wherein step (a) comprises the step of selecting the water-soluble polymer to be gelatin.

9. The method of claim 7, wherein step (a) comprises lowering the lens, concave side down, into a wet film containing the water-soluble polymer, so that a portion of the rim of the lens becomes coated.

* * * * *